(12) United States Patent (10) Patent No.: US 8,334,252 B2
Wiedemann et al. (45) Date of Patent: Dec. 18, 2012

(54) PERFUME-CONTAINING HOLLOW BODY CONSISTING OF A POLYMER MATRIX

(75) Inventors: Jörn Wiedemann, Holzminden (DE); Thorsten Hielscher, Höxter (DE); Falk Harzke, Bodenwerder (DE)

(73) Assignee: Symrise AG, Holzminden (DE)

( * ) Notice: Subject to any disclaimer, the term of this patent is extended or adjusted under 35 U.S.C. 154(b) by 201 days.

(21) Appl. No.: 12/958,821

(22) Filed: Dec. 2, 2010

(65) Prior Publication Data

US 2011/0130320 A1 Jun. 2, 2011

(30) Foreign Application Priority Data

Dec. 2, 2009 (DE) .......................... 10 2009 047 411

(51) Int. Cl.
 *A61K 8/00* (2006.01)
(52) U.S. Cl. ............................................................ 512/4
(58) Field of Classification Search .................. 510/295, 510/296, 297, 298, 438, 444; 512/4
 See application file for complete search history.

(56) References Cited

U.S. PATENT DOCUMENTS

| | | | |
|---|---|---|---|
| 3,676,199 A | 7/1972 | Hewitt et al. | |
| 6,174,577 B1 | 1/2001 | Vitorino | |
| 2005/0153135 A1* | 7/2005 | Popplewell et al. | 428/402.2 |
| 2006/0010933 A1* | 1/2006 | McGee et al. | 68/3 R |
| 2008/0268009 A1* | 10/2008 | Schuster et al. | 424/406 |
| 2012/0108888 A1* | 5/2012 | Spector | 600/27 |

OTHER PUBLICATIONS

Amazon.de: "Duftbälle", Mar. 25, 2007, XP002625429, Gefunden im Internet: URL: http://www.amazon.de/Sport-Thieme-Duftb%C3%A4lle/dp/B001C37T12/ref=sr_1_2?ie=UTF8& qid=1298964643&sr=8-2 [gefunden am Mar. 1, 2011].
Supplementary Search Report, European Application No. 10193296. 0, Mar. 14, 2011.

* cited by examiner

*Primary Examiner* — John Hardee
(74) *Attorney, Agent, or Firm* — Connolly Bove Lodge & Hutz LLP (57) ABSTRACT

The present invention concerns a perfume-containing body enclosing a single hollow space on all sides and comprising or consisting of
 an elastomeric, in particular cross-linked, polymer matrix and
 one or more perfumes stored in the polymer matrix in a total quantity of 10-75 wt. %, with reference to the total weight of the hollow body,
 optionally other substances stored in the polymer matrix, wherein
 the hollow body has a total volume of 5-8,181 cm³ at 25° C. and 1,013 mbar,
and
 the thickness of the wall surrounding the hollow space on all sides at any point is 0.25-20 mm, preferably 0.5-15 mm, particularly preferably 0.75-10 mm, most preferably 1-8 mm.

20 Claims, 1 Drawing Sheet

PERFUME-CONTAINING HOLLOW BODY CONSISTING OF A POLYMER MATRIX

CROSS-REFERENCE TO RELATED APPLICATIONS

This application claims priority under 35 U.S.C. §119(a) to Application No. 10 2009 047 411.0, filed in Germany on Dec. 2, 2009, the entire contents of which are hereby incorporated by reference.

The present invention concerns a hollow body comprising or consisting of an elastomeric polymer matrix, in which one or more fragrance substances (perfumes) and optionally other substances is or are stored, and which under the prevailing conditions of a standard laundry drying process in a laundry drier and/or of a standard dishwashing process in a dishwasher releases the fragrance substance (hereinafter: perfume) or fragrance substances (hereinafter: perfumes) and deposits it or them on the laundry or scents the air in the dishwasher, wherein the body preferably retains its structural integrity, that is to say, that it does not experience any visible damage.

The present invention also concerns the use of a hollow body comprising or consisting of to an elastomeric polymer matrix, in which one or more perfumes and optionally other substances is or are stored, for scenting laundry during a standard laundry drying process in a laundry drier and/or for scenting the air in a dishwasher during a standard dishwashing process.

The present invention further concerns a method for producing such a hollow body, which is suitable for scenting laundry during a laundry drying process in a laundry drier and/or for scenting the air in a dishwasher during a standard dishwashing process.

Details of the abovementioned aspects of the present invention and other aspects of the invention, especially particularly preferred embodiments emerge from the following description, the examples and the attached claims.

In many households and in the cleaning industry, laundry driers are being used more and more these days. Laundry driers have the advantage that the washed and still wet laundry can be dried more quickly than would be possible by drying in the air, for example. In addition, the use of laundry driers can save energy compared with drying in the living area. Through the drying process in a drier, however, it is possible for the laundry previously washed and given a pleasant scent by an appropriate detergent to then lose to this pleasant scent. However, there is a demand among consumers for laundry that is pleasantly scented after the drying process as well.

Furthermore, many households have a dishwasher. Although dishwashers perform the work of washing the dishes often perceived by consumers as time-consuming and unpleasant work by hand, dishwashing using a dishwasher still has its disadvantages. Many consumers complain that the dishwashing process results in unpleasant smells, which at the very latest only escape once the dishwasher is opened after a dishwashing process. As a result there is a demand among consumers to pleasantly scent the air escaping from the dishwasher.

In WO 2005/085404 perfume-containing objects are disclosed which also contain a fabric conditioner component and as the carrier, for example, polyamides, wherein the objects are suitable for at least 10 drying cycles in a laundry drier. Additionally, the carrier performs the task of making the object resistant to temperature loads during the drying process. The carriers used here, however, have the disadvantage that they have to have relatively high melting temperatures in order that the object does not liquefy at the temperatures during the drying process (approximately 70 to a maximum of 100° C.). In order to be able to incorporate perfume oil into such carriers, the latter must be melted at temperatures that are higher than the drying temperatures of the laundry drier. At such high melting temperatures during the production process, however, a considerable amount of the perfumes to be incorporated evaporate or a perfume oil containing perfumes undergoes chemical and/or olfactorily noticeable adverse changes. Especially desirable are objects containing perfume, which contain a high percentage of perfumes in relation to the object used. The carriers described in WO 2005/085404 are unsuitable for the production of objects containing perfume, especially for those with a high percentage of perfumes.

In WO 2005/118008, US 2005/0267231 and WO 2008/079892 compounds and objects are described which comprise a polymer matrix and an immobilized active liquid (e.g. a perfume oil), along with methods for their production and uses thereof. The polymer matrix is described as a reaction product of a polyamine with epoxy compounds, isocyanates, anhydrides or acrylates. The disclosed production method allows production without treatment at increased temperature. The embodiments of an air freshener disclosed there are described as being resilient to variations in temperature and moisture. WO 2008/079892 further states that the objects disclosed there can also be used as fabric care compositions.

The disadvantage of the objects disclosed in WO 2005/118008, US 2005/0267231 and WO 2008/079892 is that the objects described there have shown themselves in our own investigations to be insufficiently resistant to the hot, moist conditions that prevail, for example in a laundry drier (temperatures routinely in the range of 70-100° C.). In our own further investigations it was found that for example full spheres with a diameter of more than 20 mm (corresponding to a volume of approximately 4.2 $cm^3$ or more) in a polymer matrix incorporating 10 wt. % or more of perfume oil, in relation to the total weight of the object, when used in a laundry drier and/or a dishwasher were not stable. After just one, especially after three or more standard drying or dishwashing cycles (as described below) the objects described there broke in two, split, crumbled into small pieces or exhibited cracks visible with just the naked eye. After repeated use, this effect was intensified the more often the drying or dishwashing process was repeated. Here, the objects always crumbled into small pieces.

In our own corresponding investigations with full spheres, which likewise patent applications WO 2005/118008 and US 2005/0267231 or WO 2008/079892 taught, but which had a diameter of 2 cm or less, while it was observed that these did not break in two, burst and/or crumble, because of their limited size they could overall only be loaded with an inadequately small quantity of perfumes, for which reason such objects are especially unsuitable for giving off perfumes over multiple drying or dishwashing cycles in sufficient quantities, especially not over five or more standard drying or dishwashing cycles.

The essential disadvantage of such objects with limited size, apart from the low quantity of perfumes that these objects are able to contain, is also that they are impractical for consumers to use. For the consumer, a small size means that after using the object in a laundry drier or a dishwashing machine, this object must be laboriously searched for in the appliance or among the laundry. In order to increase the ease of use of the objects, objects must be provided which meet the additional requirement of consumers for a comfortable size.

The primary problem for the invention was consequently to provide an object of at least 5 cm³, which is suitable for single, in particular for multiple, use, in particular for at least five-fold use, under standard cycle conditions in a laundry drier and/or dishwasher, and which has a sufficiently high proportion by weight of one or more perfumes, wherein the object in particular after (repeated) use does not lose its structural integrity, and wherein a sufficient proportion of the perfumes is released during use, so that the laundry in the laundry drier or the air in the dishwasher is scented to a sufficient degree.

The problem is solved by a perfume-containing body enclosing a hollow space on all sides and comprising or consisting of an elastomeric, in particular cross-linked, polymer matrix and one or more perfumes stored in the polymer matrix in a total quantity of 10-75 wt. %, with reference to the total weight of the hollow body, optionally other substances stored in the polymer matrix, wherein the hollow body has a total volume of 5-8, 181 cm³ at 25° C. and 1,013 mbar, and the thickness of the wall surrounding the hollow space on all sides at any point is 0.25-20 mm, preferably 0.5-15 mm, particularly preferably 0.75-10 mm, most preferably 1-8 mm.

A hollow body according to the invention retains its structural integrity even after (repeated) use in the laundry drier or in the dishwasher and allows sufficient scenting in the respective use.

A hollow body according to the invention preferably has a total volume of 14 cm³-905 cm³, particularly preferably of 33 cm³-524 cm³. These volumes correspond approximately to a sphere diameter of 3-12 cm or 4-10 cm. In these ranges repeated use is possible without problems, the space requirement of the hollow body is generally not too high and sufficient stability and structural integrity is provided.

A hollow body according to the invention in particular has a total mass of at least 1 g, in to particular a total mass of 1-100 g, preferably of 1-50 g. The preferred total mass is extensively dependent upon the application and the dimensions of the laundry drier or dishwasher and on the number of laundry or dishwashing cycles which the hollow body according to the invention is to last for. Thus, the preferred total mass of a hollow body according to the invention, for example for use in a normal domestic dishwasher, is 1-5 g. The preferred total mass of a hollow body according to the invention, for example for use in a normal domestic laundry drier, is 1-10 g, more preferably 2-8 g. In large appliances, such as laundry driers in commercial and industrial use, the optimum total mass of a hollow body according to the invention may indeed be higher, however, for example 5-30 g.

In connection with the present invention, when substances, especially perfumes, "stored" in the polymer matrix are mentioned, this means that these substances are contained or incorporated in the polymer matrix and are not present in a form in which they constitute a surface film on the outer surface and/or the inner wall of the hollow body.

In connection with the present invention "total volume" means the external volume of the hollow body, thus the total volume of the area enclosed by the hollow body, including the wall and the hollow space enclosed by this.

Perfumes according to the invention are in particular selected from the group consisting of (details of product and brand names used in the industry):

1-phenyl-2-methyl-2-propyl acetate, 2-methyl butyl butyrate, Aldron (4-[(3,3-dimethylbicyclo[2.2.1]hept-2-yl)methyl]-2-methyl cyclohexanone), allyl-2-cyclohexyloxy glycolate, allyl-2-pentyloxy glycolate, allyl-3-cyclohexyl propionate, allyl capronate, Amarocit (1,1-dimethoxy-2,2,5-trimethyl-4-hexene), Ambral (dodecahydro-3,8,8,11a-tetramethyl-5H-3,5a-epoxynaphth[2,1-c]oxepine), Ambrettolid (9-hexadecen-16-olide), Ambrinol S (1,2,3,4,4a,5,6,7-octahydro-2,6,6-trimethyl-2-napthalinol), Ambrinolepoxid, Ambrocenide (4aR,5R,7aS,9R)-octahydro-2,2,5,8,8,9a-hexamethyl-4H-4a,9-methanoazuleno(5,6-d)-1,3-dioxol), Ambroxid (3a,6,6,9a-tetramethyldodecahydronaphtho[2,1-b]-furan), amyl formate, Aurelione (7-cyclohexadecen-1-one and 8-cyclohexadecen-1-one), Boronal [2-methyl-4-(2,6,6-trimethyl-1-cyclohexen-1-yl)-butenal], Brahmanol [2-methyl-4-(2,2,3-trimethyl-3-cyclopentenyl)-butanol], Buccoxime (1,5-dimethylbicyclo[3.2.1]octan-8-onoxim), butyl acetate, Cantryl (2,2,3-trimethyl-3-cyclopentenyl-1-acetonitrile), Cassix 150 (4-methoxy-2-methyl-2-butanethiol), Chrysantheme [1-(2,4-dimethyl-3-cyclohexen-1-yl)-2,2-dimethyl-1-propanone], cis-3-hexenyl acetate, citronellyl butyrate, citronellyl tiglinate (3,7-dimethyl-6-octenyl-2-methyl crotonate), citronitrile (3-methyl-5-phenyl-2-pentene nitrile), Citrowanil B (alpha-ethenyl-alpha-methyl-benzene proprane nitrile), Claritone (2,4,7-tetramethyl-6-octen-3-one), Corps Racine VS [2-(3-phenylpropyl)pyridine], Coumarone (1-(2-benzofuranyl)-ethanone), Cyclogalbanate (allyl cyclohexyl oxyacetate), cyclohexylmagnol (alpha-methyl-cyclohexane propanol), Datilat (1-cyclohexylethyl crotonate), ethyl-2-methyl butyrate, ethyl isobutyrate, ethyl isovalerate, ethyltricyclo[5.2.1.0$^{2,6}$]decan-2-yl carboxylate, Farenal (2,6,10-trimethyl-9-undecenal), Filbertone (5-methyl-2-hepten-4-one), Fleursandol (4-(3a,4,5,6,7,7a-hexahydro-4,7-methano-1H-inden-6-yl)-3-methyl-3-buten-2-ol), Florazon (4-ethyl-alpha,alpha-dimethyl benzene propanal), Floropal (2,4,6-trimethyl-4-phenyl-1,3-dioxane), Fragolane [(2,4-dimethyl-[1,3]dioxolan-2-yl)acetic acid ethyl ester)], Frutinat (but-2-ene acid-1,3-dimethyl butyl ester), gamma-decalactone, geranyl acetate, geranyl butyrate, geranyl tiglinate (trans-3,7-Dimethyl-2,6-octadienyl-2-methyl crotonate), Globalide [(11/12)-pentadecen-15-olide], Globanone (8-cyclohexadecen-1-one), hexyl butyrate, hydrocitronitrile (beta-methylbenzene pentane nitrile), Indianol (4-[3a,4,5,6,7,7a-hexahydro-4,7-methano-1H-inden-5(6)-yl]-3-methyl-3-buten-2-ol), Indoflor (4,4a,5,9b-Tetrahydroindeno[1,2-d]-m-dioxin), Irisnitrile (2-nonenylnitrile), isoamylacetate, isoamylisovalerianate, isodamascone [1-(2,4,4-trimethyl-2-cyclohexen-1-yl)-2-buten-1-one], isomuscone (cyclohexadecanone), Jacinthaflor (2-methyl-4-phenyl-1,3-dioxolane), Ketamber (dodecahydro-3,8,8,11a-tetramethyl-5H-3,5a-epoxynaphth[2,1-c]oxepine), lactojasmone (4-hexyl-4-methyl-butyrolactone), leguminal (propanal-methyl-cis-3-hexenyl-acetal), macrolide (oxacyclohexadecan-2-one), madranol (mixture of various hexahydro methylionones), Magnolan (2,4-dimethyl-5,6-indeno-1,3-dioxane), Majantol [2,2-dimethyl-3-(3-methylphenyl)-propanol], Mandaril (3,12-tridecadiennitrile), menthyl acetate, methyl butyrate, methyl dihydrojasmonate, methyl isobutyrate, mintonat (3,3,5-trimethylcyclohexyl acetate), Mugetanol [1-(4-isopropyl cyclohexyl)-ethanol], nerolione [1-(3-methyl-2-benzofuranyl)-ethanone], octyl acetate, Ozonil (2-tridecene nitrile), palisandal (1,1-dimethoxycyclododecane), Palisandin (cyclododecylmethylether), Parmanyl [3-(cis-3-hexenyloxy)-propane nitrile], Passifloran (3-acetylthiohexyl acetate), Peacholide (cis- and trans-3-methyl-gamma-decalactone), prenyl salicylate, Profarnesal (2,6,10-trimethyl-5,9-undecadienal), Projasmon P (2-heptylcyclopentanone), Pyroprunat (but-2-ene acid bicyclopenten-2-yl ester), rholiate (carbonic acid-ethyl-2,3,6-trimethylcyclohexyl ester), Rosaphene (2-methyl-5-phenylpentan-1-ol), rose oxide, Sandel 80 (trans-3-isocamphylcyclohexanol), Sandranol (2-ethyl-4-(2,2,3-trimethyl-3-cyclpenten-1-yl)-2-buten-1-ol), Symrose (4-isoamylcyclohexanol), Symroxane (4-(3-methyl butyl)-cyclohexanol (Z)), Tabanon [4-(2-butenyliden)-3,4,5-trimethyl-2-cyclohexen-1-one], terpineol-4, Timberol (2,2,6-trimethyl-alpha-propyl-cyclohexane propanol), tolylacetaldeyde D para (4-methyl-benzene acetaldehyde), tricyclodecenyl propionate, Tropicol (2-mercapto-2-methyl-pentan-1-ol), Vertosine [2-(2,4-(or 3,5)-dimethyl-3-cyclohexen-1-yl)-methylene aminobenzoic acid methyl ester], Vertral (octahydro-4,7-methano-1H-indene carbaldehyde), Vetikol acetate (1,3-dimethyl-3-phenyl butyl acetate), Vetival (4-cyclohexyl-4-methylpentan-2-one), Ysamber K (spiro hexahydro-1',1',5',5'-tetramethyl-[1,3-dioxolan-2,8'-(5'H)-[2H-2,4a]-methanonaphthalene].

Further preferred perfumes, stored in hollow bodies according to the invention are mentioned in S. Arctander, Perfume and Flavor Materials, Vol. I and II, Montclair, N.J. 1969, author's edition, or K. Bauer et al., Common Fragrance and Flavor Materials, 5th Edition, Wiley-VCH, Weinheim 2006.

Particularly preferred hollow bodies according to the invention contain in particular extracts of natural raw materials such as essential oils, concretes, absolutes, resins, resinoids, balsams and tinctures, such as for example ambergris tincture; amyris oil; angelica seed oil; angelica root oil; anise oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cede oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lavage oil; distilled lime oil; pressed lime oil; linaloe oil; litsea cubeba oil; bayleaf oil; mace oil; marjoram oil; mandarin oil; massoi bark to oil; mimosa absolute; musk seed oil; musk tincture; clary sage oil; nutmeg oil; myrrh absolute; myrrh oil; bay oil; clove leaf oil; clove flower oil; neroli oil; olibanum absolute; olibanum oil; opopanax oil; orange-flower absolute; orange oil; origanum oil; palmarosa oil; patchouli oil; perilla oil; peruvian balsam oil; parsley leaf oil; parsley seed oil; petitgrain oil; peppermint oil; pepper oil; pimenta oil; pine oil; pennyroyal oil; rose absolute; rosewood oil; rose oil; rosemary oil; dalmation sage oil; Spanish sage oil; sandalwood oil; celery seed oil; spike lavender oil; Japanese anise oil; styrax oil; tagetes oil; fir needle oil; teatree oil; turpentine oil; thyme oil; tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom.

In a further preferred hollow body according to the invention this contains one, two or more perfumes in the form of individual perfumes selected from the group of hydrocarbons. Particularly preferred individual perfumes to be used from the group of hydrocarbons are for example 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane; aliphatic alcohols, such as for example hexanol; octanol; 3-octanol; 2,6-dimethyl-heptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal-diethylacetal; 1,1-dimethoxy-2,2,5-trimethyl-4-hexene; citronellyl oxyacetaldehyde; 1-(1-methoxy-propoxy)-(E/Z)-3-hexene; aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one; aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol; aliphatic nitriles, such as for example 2-nonenenitrile; 2-undecenenitrile; 2-tridecenenitrile; 3,12-tridecenenitrile; 3,7-dimethyl-2,6-octadienenitrile; 3,7-dimethyl-6-octenenitrile; aliphatic carboxylic acid esters, such as for example (E)- and (Z)-3-hexenylformate; ethyl acetoacetate; isoamyl acetate; hexyl acetate; 3,5,5-trimethyl-hexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate; 4-methyl-2-pentyl-crotonate; acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof; acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl- and diethylacetals of geranial, neral and 7-hydroxy-3,7-dimethyloctanal; cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof; cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methononaphthalen-8(5H-)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (cedryl methyl ketone); cyclic alcohols, such as, for example, 4-tert.-butylcyclohexanol; 3,3,5-trimethylcyclohexanol; 3-isocamphylcyclohexanol; 2,6,9-trimethyl-Z2,Z5, E9-cyclododecatrien-1-ol; 2-isobutyl-4-methyltetrahydro-2H-pyran-4-ol; cycloaliphatic alcohols, such as, for example, alpha,3,3-trimethylcyclo-hexyl-methanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol; cyclic and cycloaliphatic ethers, such as, for example, cineole; cedryl methyl ether; cyclododecyl methyl ether; 1,1-dimethoxycyclododecane; (ethoxymethoxy)cyclododecane; alpha-cedrene epoxy resin; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methyl-propyl)-1,3-dioxan; cyclic and macrocyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclo-hexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone; cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde; cycloaliphatic ketones, such as, for example, 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl)ketone; esters of cyclic alcohols, such as, for example, 2-tert.-butylcyclohexyl acetate; 4-tert.-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenylpropionate; 4,7-methano-3a,4,5,6,7,7a-hexahydro-5 or 6-indenyl isobutyrate; 4,7-methanooctahydro-5 or 6-indenyl acetate; the esters of cycloaliphatic alcohols such as for example 1-cyclohexylethyl crotonate; esters of cycloaliphatic carboxylic acids, such as, for example, allyl 3-cyclohexyl-propionate; allyl cyclohexyl oxyacetate; cis- and transmethyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate; araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol; esters of araliphatic alcohols and aliphatic carboxylic acids, such as, for example, benzyl acetate; benzylpropionate; benzyl isobutyrate; benzyl isovalerate; 2-phenylethyl acetate; 2-phenylethylpropionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin; aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanol; 2-methyl-3-(4-isobutylphenyl)propanol; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)propanal; 2-methyl-3-(4-methylendioxyphenyl)propanal; aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-d hydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone; aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate;

methyl 2,4-dihydroxy-3,6-dimethylbenzoate; ethyl 3-phenylglycidate; ethyl 3-methyl-3-phenylglycidate; nitrogen-containing aromatic compounds, such as, for example, 2,4,6-trinitro-1,3-dimethyl-5-tert-butylbenzene; 3,5-dinitro-2,6-dimethyl-4-tert.-butylacetophenone; cinnamonitrile; 3-methyl-5-phenyl-2-pentenonitrile; 3-methyl-5-phenyl pentanonitrile; methyl anthranilate; methyl-N-methylanthranilate; Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde; 6-isopropylquinoline; 6-isobutylquinoline; 6-sec-butylquinoline; 2-3(phenylpropyl)pyridine; indole; skatole; 2-methoxy-3-isopropylpyrazine; 2-isobutyl-3-methoxypyrazine; phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate; heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

The embodiments of the invention mentioned in the following, especially (particularly) preferred designs and embodiments, solve the problem posed to an exceptional extent. The (especially) preferred hollow bodies according to the invention possess in use, including in repeated use respectively, in a laundry drier or dishwasher a particularly high stability and structural integrity and perfume the laundry or the air of the dishwasher to an adequate extent.

A particularly good structural integrity of a hollow body according to the invention is to achieved if the polyamines (especially the polyamide polyamines mentioned below), cross-linkers and/or stabilizers, indicated as (particularly) preferred are used especially in each case in the proportions specified as preferred.

The hollow bodies according to the invention in the (particularly) preferred embodiments, over repeated cycles also demonstrate an essentially even olfactory profile, particularly in direct comparison following two consecutive drying or dishwashing cycles. This is especially the case if the perfumes indicated as (particularly) preferred, are used in the proportions specified as preferred.

In particular, a hollow body according to the invention is suitable for use, preferably for repeated use, in a laundry drier and/or in a dishwashing machine (embodiment 1).

In a preferred embodiment, a hollow body according to the invention after 5 or more, in particular after 10 or more, standard drying cycles in a laundry drier or after 10 or more standard dishwashing cycles in a dishwasher exhibits no notable, in particular absolutely no, structural damage, i.e. the hollow body withstands said cycles with its structural integrity extensively, in particular completely, intact (embodiment 2).

In connection with the present invention "structural integrity" means that the object under investigation or the hollow body according to the invention after single or repeated use in a laundry drier or a dishwasher has essentially experienced no damage, in particular no damage at all, which is visible with the naked eye. The preference is for hollow bodies according to the invention which under ten times magnification, for example with a light microscope, have essentially experienced no damage, in particular no damage at all, which is visible.

In connection with the present invention, a standard drying cycle of a laundry drier and a standard dishwashing cycle of a dishwasher are defined as follows:

Standard Drying Cycle of a Laundry Drier:

4.5 kg terry towels in 90% cotton and 10% viscose, which have first been washed at 95° C. with a commercially available liquid detergent and spun at 1,100 rpm, are placed in the Miele Softronic T4222C laundry drier and dried with the "cupboard dry" temperature program (drier outlet temperature: 75° C.).

Standard Dishwashing Cycle of Dishwasher:

Bosch Super Silence auto 3 in 1 ("Auto 55-65° C." temperature program); total duration of a standard dishwashing cycle=approximately 2 hours and 19 minutes.

In preferred embodiments, the present invention concerns a hollow body, in particular according to one of the above-mentioned embodiments, wherein in the elastomeric polymer matrix as additional substances one or more stabilizers in a quantity of 5-60 wt. %, in particular 10-60 wt. %, more preferably 20-55 wt. %, particularly preferably 30-50 wt. %, are stored, in each case with reference to the total weight of the hollow body (embodiment 3).

Stabilizers that are used particularly preferably are colored stabilizers or substances with certain surface characteristics. These particularly preferred stabilizers thus have a positive effect on the appearance and texture of the hollow body according to the invention, e.g. the color or texture of the surface of the hollow body.

Preferred hollow bodies according to the invention are hollow bodies according to embodiment 3, wherein the, one, more or all the stabilizers is or are pourable at 25° C. and 1,013 mbar and has or have a boiling point of greater than or equal to 180° C. at 1,013 mbar, in particular a boiling point of greater than or equal to 220° C. at 1,013 mbar, preferably a boiling point of greater than or equal to 250° C. at 1,013 mbar, (embodiment 4).

In connection with the present invention "pourable" means liquid and viscous, as well as pasty, in particular liquid. However, "pourable" also means that a liquid, free-flowing, pourable or flowable mass or liquid can contain a proportion of solids provided that they can be poured.

More preferred hollow bodies according to the invention are hollow bodies according to embodiment 3 or 4, wherein the, one, more or all the stabilizers is or are selected from the group comprising phthalic acid esters, paraffins and polyalkylene glycols, polyalkylene glycol ethers and polyalkylene glycol esters (embodiment 5).

Particularly preferred hollow bodies according to the invention are hollow bodies according to one of embodiments 3 to 5, wherein the, one, more or all the stabilizers is or are selected from the group consisting of:

phthalic acid esters, in particular diethyl phthalate and dibutyl phthalate, and/or paraffins, in particular isoparaffins, preferably isoparaffins with a boiling point of 270 and 310° C. at 1,013 mbar and/or polyalkylene glycols, polyalkylene glycol ethers or polyalkylene glycol esters (embodiment 6).

The polyalkylene glycols, their ethers or their esters, in particular have the following formula:

wherein:
n=an integer between 1 and 50,
R═H or methyl,
R'═H, $C_1$-$C_4$-alkyl, acetyl, phenyl,
R"═H, $C_1$-$C_4$-alkyl, acetyl, phenyl (embodiment 6a).

In connection with the invention polyalkylene glycols, their ethers or their esters are preferred which correspond to the above formula, wherein:
n=1, 2 or 3,
and/or
R=methyl,
and/or
R'=$C_1$-$C_4$-alkyl,
and/or
R"═H, $C_1$-$C_4$-alkyl.

In connection with the invention as stabilizers particular preference is for polyalkylene glycol ethers, since these bring about a particularly good stability and structural integrity of a hollow body according to the invention (embodiment 6b).

In connection with the invention further preference is for polyalkylene glycol ethers according to the above formula, wherein:
n=2 or 3,
R=Me,
R'=$C_1$-$C_4$-alkyl,
and
R"═H, $C_1$-$C_4$-alkyl (embodiment 6c).

Quite particularly preferred hollow bodies according to the invention are hollow bodies according to one of embodiments 3-6, wherein the, one, more or all the stabilizers is or are selected from the group consisting of butyl diglycol, dipropylene glycol-n-propyl ether, propylene glycol phenyl ether, dipropylene glycol monomethyl ether, tripropylene glycol monomethyl ether, dipropylene glycol-n-butyl ether and tripropylene glycol-n-butyl ether (embodiment 7).

Stabilizers which are selected from the group consisting of phthalic acid esters, paraffins and polyalkylene glycols, their ethers or esters, are particularly preferred for the invention, since if these are in a hollow body according to the invention, in drying cycles of laundry driers and/or dishwashing cycles of dishwashers they do not evaporate or only to a minor extent. Evaporation could lead to stresses in the hollow body. In addition, through evaporation of stabilizers stresses, arising from a reduction in the proportion of perfumes due to them being given off in the laundry or the air, would be further intensified.

According to the invention, all stabilizers can be used which dissolve in the polyamine of the matrix in the perfumes, which are usually present in the form of a perfume oil.

Similarly preferable hollow bodies according to the invention are hollow bodies according to embodiment 3, wherein the, one, more or all the stabilizers is or are solid at 25° C. and 1,013 mbar and selected from the group consisting of clay minerals and inorganic pigments (embodiment 8).

A hollow body according to the invention can contain non-transparent stabilizers. Through the use of these non-transparent stabilizers these embodiments of the hollow body according to the invention are no longer formulated to be clear or transparent.

More preferred hollow bodies according to the invention are hollow bodies according to embodiment 8, wherein the, one, more or all the stabilizers is or are selected from the group consisting of talcum, chalk, calcium sulfate, calcium carbonate, bentonite, zinc oxide, titanium dioxide and montmorillonite (embodiment 9).

Stabilizers used quite particularly preferably according to the invention are stabilizers with small grain sizes, such as for example talcum, chalk, zinc oxide or titanium dioxide. Further quite particularly preferred stabilizers are those stabilizers which are economically advantageous raw materials.

Preferred hollow bodies according to the invention, in particular hollow bodies according to one of the preceding embodiments, are characterized by the fact that as a further substance or further substances one or more additive substances in a quantity of 0.5-5 wt. %, in particular 1-3 wt. %, in each case with reference to the total weight of the hollow body, is (are) stored in the elastomeric polymer matrix of the hollow body, and selected from the group consisting of:
dyes,
glitter, and
substances that are suitable for masking, neutralizing and/or preventing bad olfactory impressions, but which do not have any inherent smell, in particular here cyclodextrins (embodiment 10).

Preferred hollow bodies according to the invention, in particular hollow bodies according to one of the preceding embodiments, are characterized by the fact that these contain 2, 3, 4, 5, 6, 7, 8, 9, 10 or more perfumes, in particular a perfume oil (embodiment 11).

Preferred hollow bodies according to the invention, in particular hollow bodies according to one of the preceding embodiments, are characterized by the fact that the total quantity of the perfumes stored in the elastomeric polymer matrix is 10-50 wt. %, preferably 10-40 wt. % and particularly preferably 15-30 wt. %, in each case with reference to the total weight of the hollow body (embodiment 12).

Preferred hollow bodies according to the invention, in particular hollow bodies according to one of the preceding embodiments, are characterized by the fact that at least one, in particular two, more preferably three or more of the perfumes has (have) a log-$K_{o/w}$ value of less than 4 (embodiment 13).

The log-$K_{o/w}$ value is a measure of the polarity of a substance. The log-$K_{o/w}$ designates the log 10 of the distribution coefficient of a substance between 1-octanol (non-polar) and water (polar).

In practice, the log-$K_{o/w}$ value is determined by calculation, with the respective molecular structure of the substance whose log-$K_{o/w}$ value is to be determined being used as a basis. In the context of the present text, the term "log-$K_{o/w}$ value" designates the value calculated on the basis of the respective molecular structure using the "EPIWIN" software program of P. Howard and W. Meylan [Version 2.2]. This software program can be obtained from Syracuse Research Corporation, Merrill Lane, Syracuse, N.Y. 13210, USA.

Perfumes with a log-$K_{o/w}$ value of less than 4 can only be transferred to a product in an aqueous process with great difficulty. In an aqueous process, such as for example laundry washing, laundry drying or in a dishwasher, because of their polarity these perfumes are washed away with the water. Perfumes with a log-$K_{o/w}$ value preferably used for the hollow bodies according to the invention are selected from the group consisting of (details of product and brand names used in the industry are given in some cases): FRUCTATE®, MALTOL, ACETALDEHYDE, ETHYL MALTOL, PHENOXYETHYL ALCOHOL, ANISE ALCOHOL, JASMAPRUNAT, ETHYL PROPIONATE, FRAMBINON®, COUMARIN, ETHYL VANILLIN, OCTAHYDROCOUMARIN, CIS-3-HEXENOL, VANILLIN, ANISYLNITRILE, FRAGO- LANE®, JACINTHAFLOR®, ACETANISOL, HELIOTROPIN, INDOFLOR®, CINNAMYL ALCOHOL, CINNAMYL NITRILE, PHENYL ETHYL ALCOHOL, FLOROSA, BUCCOXIME®, FILBERTONE, METHYL ANTHRANILATE, HELIONAL, NEROLIONE, HYDROXYCITRONELLOL, DELTA-DECALACTONE, GAMMA-DECALACTONE, OCTENOL-1,3, CIS-3-HEXENYL ACETATE, THUJONE, ISOEUGENOL, MAGNOLAN, CYCLOGALBANAT®, EUGENOL, MANZANATE, VETIKON®, LIGUSTRAL, VERTOCITRAL, ISOBORNEOL, FENCHOL, BORNEOL, BETA-METHYL NAPHTHYL KETONE, MENTHONE, ISOMENTHONE, HEDIONE, PEACHOLIDE, ALDEHYDE C16 SO-CALLED, PHENIRAT®, MELONAL®, IRISNITRILE, FLOROPAL, VERTACETAL®, HERBAFLORAT, EVERNYL (methyl-2-4-dihydroxy-3-6-dimethyl benzoate), NEROLIN YARA YARA, CITROWANIL® B, ALPHA-TERPINEOL, CANTRYL®, FRESCOLAT® ML (MENTHYL LACTATE), LINALOOL, L-MENTHOL, ANETHOL, CITRAL, ROSAPHEN®, GERANIOL, MAJANTOL®, L-CITRONELLOL, CIS-ROSE OXIDE, MUGETANOL, VETIVAL®, SYMROSE®.

Preferred hollow bodies according to the invention, in particular hollow bodies according to one of the preceding embodiments, are characterized by the fact that the, one, more or all of the perfumes stored is or are selected from the group consisting of FRUCTATE®, MALTOL, ACETALDEHYDE, ETHYL MALTOL, PHENOXYETHYL ALCOHOL, ANISE ALCOHOL, JASMAPRUNAT, ETHYL PROPIONATE, FRAMBINON®, COUMARIN, ETHYL VANILLIN, OCTAHYDROCOUMARIN, CIS-3-HEXENOL, VANILLIN, ANISYLNITRILE, FRAGOLANE®, JACINTHAFLOR®, ACETANISOL, HELIOTROPIN, INDOFLOR®, CINNAMYL ALCOHOL, CINNAMYL NITRILE, PHENYL ETHYL ALCOHOL, FLOROSA, BUCCOXIME®, FILBERTONE, METHYL ANTHRANILATE, HELIONAL, NEROLIONE, HYDROXYCITRONELLOL, DELTA-DECALACTONE, GAMMA-DECALACTONE, OCTENOL-1,3, CIS-3-HEXENYL ACETATE, THUJONE, ISOEUGENOL, MAGNOLAN, CYCLOGALBANAT®, EUGENOL, MANZANATE, VETIKON®, LIGUSTRAL, VERTOCITRAL, ISOBORNEOL, FENCHOL, BORNEOL, BETA-METHYL NAPHTHYL KETONE, MENTHONE, ISOMENTHONE, HEDIONE, PEACHOLIDE, ALDEHYDE C16 SO-CALLED, PHENIRAT®, MELONAL®, IRISNITRILE, FLOROPAL, VERTACETAL®, HERBAFLORAT, EVERNYL (methyl-2-4-dihydroxy-3-6-dimethyl benzoate), NEROLIN YARA YARA, CITROWANIL® B, ALPHA-TERPINEOL, CANTRYL®, FRESCOLAT® ML (MENTHYL LACTATE), LINALOOL, L-MENTHOL, ANETHOL, CITRAL, ROSAPHEN®, GERANIOL, MAJANTOL®, L-CITRONELLOL, CIS-ROSE OXIDE, MUGETANOL, VETIVAL®, SYMROSE® (embodiment 14).

Preferred hollow bodies according to the invention, in particular hollow bodies according to one of the preceding embodiments, are characterized by the fact that the hollow body after 5 standard drying cycles of a laundry drier or after 5 standard dishwashing cycles of a dishwasher still contains 40 wt. % or more of the total quantity of perfumes originally present in the hollow body (embodiment 15).

Preferred hollow bodies according to the invention, in particular hollow bodies according to one of the preceding embodiments, are characterized by the fact that that a maximum of 25 wt. % of the total quantity of the perfumes originally present in the hollow body have a Kovats index of <1,500 (embodiment 16).

The proportion of perfumes or perfume oil in the hollow body according to the invention is selected by the person skilled in the art according to the desired scent intensity. In particular, the proportion of perfumes or of perfume oil, containing the perfume(s), in the hollow body according to the invention is selected so that the quantity of perfumes that is applied to the laundry during a drying process of a laundry drier is suitable for providing the laundry with a scent.

Preferred hollow bodies according to the invention, in particular hollow bodies according to one of the preceding embodiments, are characterized by the fact that for each standard laundry drying or standard dishwashing cycle 50 mg or more of perfumes are released (embodiment 17).

Such a quantity is sufficient to scent the laundry in a laundry drier or the air in a dishwasher.

Preferred hollow bodies according to the invention, in particular hollow bodies according to one of the preceding embodiments, are characterized by the fact that the hollow body is seamless and/or has the shape of a sphere, a cube, a cylinder, a cone, a cuboid, an ellipsoid or a sphere-like shape, with spheres and sphere-like shapes being preferable (embodiment 18).

In connection with the present invention, "seamless" means without a seam or visible joining line. It also means that the hollow body according to the invention is not produced by producing two separate parts which are then joined together afterwards by means of a weld, fusing or the like.

A quite particular preference for a hollow body according to the invention is for the shape to be a (seamless) hollow sphere.

The invention also, however, includes complex shapes such as fish, stars or die. But the preference is for shapes of the hollow body according to the invention which are less complex. Less complex shapes, such as the shape of a hollow sphere, result in a more even layer thickness for the hollow body. A more even layer thickness has the advantage that the danger of the shape cracking is minimized.

A quite particular preference for the hollow body according to the invention is for the shape to be a hollow sphere, because as a result of the very even layer thickness fewer stresses can arise. A hollow body according to the invention in the shape of a hollow sphere is a particularly stable hollow body within the meaning of the invention.

A further advantage of the shape of a hollow sphere is that as a result of the even layer thickness an essentially steadier release of the perfumes is possible. With a comparable hollow body in the shape of a solid sphere, that is to say, a sphere that is not hollow inside, apart from the problem of splitting or cracking, there is the added disadvantage that the volatile active substances are not given off steadily, since to some extent they have further to travel from the inside of the sphere to the edge.

Preferred hollow bodies according to the invention, in particular hollow bodies according to one of the preceding embodiments, are characterized by the fact that the elastomeric polymer matrix is cold cross-linked (embodiment 19).

Preferred hollow bodies according to the invention, in particular hollow bodies according to one of the preceding embodiments, are characterized by the fact that the elastomeric polymer matrix is or contains the reaction product i) of a cross-linker from the group consisting of epoxy resins, isocyanates, anhydrides or acrylates
with
ii) one, two or more polyamines (embodiment 20).

Preferred hollow bodies according to the invention, in particular hollow bodies according to one of the preceding embodiments, are characterized by the fact that the elastomeric polymer matrix is or contains the reaction product of
i) 2-5 wt. % of a cross-linker from the group consisting of epoxy resins, isocyanates, anhydrides or acrylates, in particular 2-5 wt. % of a cross-linker from the group consisting of isocyanates,
with
ii) a total of 10-35 wt. %, in particular 15-30 wt. % of one, two or more polyamines,
wherein the percentages by weight in each case are with reference to the total weight of the hollow body (embodiment 21).

In certain embodiments of the hollow body according to the invention, the polymer matrix is formed with a substance with at least one epoxy resin group as the cross-linking component. According to the invention, the cross-linking component for producing a hollow body according to the invention, if the cross-linking component is an epoxy component, preferably has a plurality of epoxy groups.

Particularly preferably, for the production of a polymer matrix for a hollow body according to the invention an epoxy component is used which at room temperature and 1,013 mbar is in liquid form. Preferably used epoxy resins are listed in the "Handbook of epoxy resins" by Henry Lee and Kris Neville (McGraw Hill, 1967); "The Epoxy Formulators Manual" of the Society of Plastics Industry, Inc. (1984); and the "Encyclopedia of Science and Technology" (Kirk-Othmer, John Wiley & Sons, 1994).

Quite particularly preferred epoxy resins as the starting materials for the production of a polymer matrix for a solid body according to the invention are diglycidyl esters of bisphenol A and F (obtainable as EPON 828 and EOIB 8620 from Resolution Performance Products), hydrogenated glycidyl ethers of bisphenol A (obtainable as EPALLOY 5000 and EPALLOY 5001 from CVE Speciality Chemicals) and the diglycidyl ethers of butanediol, dimethanolcyclohexane, neopenthylglycol and trimethylpolypropane (all available in the HELOSY Modifier range from Resolution Performance Products).

In certain embodiments of the hollow body according to the invention, the polymer matrix is produced with a cross-linking component, containing at least one functional isocyanate group. According to the invention, such an isocyanate cross-linking component preferably contains a plurality of isocyanate groups and corresponds to a polyisocyanate. A further preference is for the isocyanate cross-linking component to be fluid at 25° C. and 1,013 mbar.

Particularly preferred isocyanates in connection with this invention are aliphatic difunctional isocyanates (for example, isophorone diisocyanate or bis(4-isocyanatocyclohexyl) methane.

A quite particular preference for the production of a polymer matrix of a hollow body according to the invention is for polyfunctional isocyanates with a temperature of ebullition of over 180° C. at 1,013 mbar and low toxicity. Examples of these quite particularly preferred polyfunctional isocyanates are the DESMODUR range of products available from Bayer. Within the DESMODUR range the DESMODUR N range of aliphatic isocyanates is particularly preferred, and here particularly DESMODUR N-3300 and N-3800, as well as the DESMODUR Z range, here in particular DESMODUR Z4470.

In certain embodiments of the hollow body according to the invention, the polymer matrix is produced with a cross-linking component, which has at least one functional anhydride group. Anhydrides used by preference have a plurality of functional anhydride groups (polyanhydrides). Further preference is for the use of anhydrides which are in liquid form at 25° C. and 1,013 mbar.

Cross-linking components used quite particularly preferably for the production of a polymer matrix for a solid body according to the invention are anhydrides, which are synthetic substances, which are not based on maleic acid.

In certain embodiments of the hollow body according to the invention, the latter contains a polymer matrix, in the production of which the cross-linking component is a substance with at least one functional acrylate group. Acrylates used by preference as cross-linking components have a plurality of acrylate groups (polyacrylates). Quite particular preference is for the use of polyacrylates within the meaning of the invention, if these are liquid at 25° C. and 1,013 mbar.

All epoxy resins, isocyanates, anhydrides and acrylates are indicative and the execution of the invention is not limited to these.

Further preferred hollow bodies according to the invention are hollow bodies according to embodiment 20 or 21, characterized by the fact that the, one, both or more of the polyamines is or are a polyamide-polyamine, in particular a polyamide-polyether-blockpolymer-polyamine (embodiment 22).

Particularly preferred hollow bodies according to the invention are hollow bodies according to one of the embodiments 20-22, characterized by the fact that the, one, both or more of the polyamines is or are pourable, in particular liquid, at 25° C. and 1,013 mbar (embodiment 23).

More particularly preferred hollow bodies according to the invention are hollow bodies according to one of the embodiments 20-23, characterized by the fact that the, one, both or more of the polyamines is or are aliphatic (embodiment 24).

Polyamines or mixtures of polyamines to be used quite particularly preferably for the invention are non-aromatic.

Quite particularly preferred hollow bodies according to the invention are hollow bodies according to one of the embodiments 20-24, characterized by the fact that the average molecular weight $M_W$ of the total quantity of the ii) polyamines is 5,000-15,000 g/mol (embodiment 25).

Even more particularly preferred hollow bodies according to the invention are hollow bodies according to one of the embodiments 20-25, characterized by the fact that ii) has two or more different polyamines, wherein at least one polyamine has an average molecular weight $M_W$ of 5,000-8,000 g/mol and at least one further polyamine has an average molecular weight $M_W$ of 9,000-12,000 g/mol (embodiment 26).

Examples of polyamines to be used according to the invention are JEFFAMINE D-230, T-403 or XTJ-511 from the Huntsman Corporation. Further polyamines for use according to the invention are cycloaliphatic diamines, such as isophorone diamine (IPDA), aminoethylpiperazine and 1,3-bis (aminomethyl)cyclohexane (1,3-BAC) and polyamines of the polyamidoamine family, such as the UNIREZ range from Arizona Chemicals.

Furthermore, for the present invention, use can be made of the polyamines described in patent applications WO 2005/118008, US 2005/0267231 and/or WO 2008/079892 and/or in U.S. Pat. No. 6,870,011 and/or U.S. Pat. No. 6,399,713, which hereby expressly by way of reference become part of the present application and the (preferred or particularly preferred) embodiments. The polyamines mentioned there as preferable, in particular the polyamide polyamines mentioned there, and the cross-linkers mentioned there, are expressly and in each case explicitly preferable in connection with the present invention. In particular, the polyamines and cross-linkers explicitly described and preferred in WO 2005/118008, US 2005/0267231 and WO 2008/079892 are in connection with the present invention likewise preferable, since with these polyamines and/or cross-linkers the object on which the invention is based can be achieved to a particular extent.

For the production of a polymer matrix of a hollow body according to the invention, the polyamine can also be in the form of a mixture of two or more polyamines. When selecting the mixture of certain polyamines the person skilled in the art can influence the viscosity, the hardening time and the product characteristics. Advantageous polyamine mixtures are easily recognizable to the person skilled in the art and furthermore examples of polyamine mixtures are disclosed in the examples below.

Perfume-containing hollow bodies according to the invention can be characterized by the fact that the polyamide polyamine(s) is or are produced from non-aromatic di- or triamines, preferably from primary di- or triamines or secondary diamines, more preferably from primary polyalkyleneoxydi- or triamines, here in particular with a molecular weight of 200-5,000 daltons, or piperazine.

Perfume-containing hollow bodies according to the invention can also be characterized by the fact that the polyamine(s) is or are a polyamide-polyether-block-polymer-polyamine, which is the reaction product of one or more polyalkylenoxy-polyamines with one or more aliphatic polyacid(s).

Polyacids used by preference here are selected from the group consisting of dimerized oleic acid, 1,4-cyclohexane dicarbonic acid, hydrogenated dimeric acid and adipinic acid.

In a perfume-containing hollow body according to the invention, the volume of the hollow space as a proportion of the total volume of the hollow body is in a range between a multiple of the volume of the polymer matrix and a proportion of the volume of the polymer matrix.

Preferred hollow bodies according to the invention, in particular hollow bodies according to one of the preceding embodiments, are characterized by the fact that the volume of the hollow space is 40 vol. %-98 vol. %, preferably 70 vol. %-95 vol. %, with reference to the total volume of the perfume-containing hollow body at 25° C. and 1,013 mbar (embodiment 27).

A use according to the invention of a hollow body according to the invention, in particular in a configuration of one of the preceding embodiments 1-27, consists of the application of a scent to laundry during a drying process in a laundry drier and/or of the scenting of the air in the dishwasher during a dishwashing process, wherein the hollow body according to the invention is suitable for repeated use.

A preferred use according to the invention is characterized by the fact that the hollow body after repeated use (in particular after 5 or more, preferably after 10 or more standard cycles) has extensive or complete structural integrity.

A method according to the invention for producing a hollow body according to the invention, in particular according to one of the preceding embodiments 1-27, comprises or consists of the following steps:

a) preparation of one or more reagents for producing an elastomeric, in particular cross-linked, polymer matrix;
b) addition of 10-75 wt. % of one or more perfumes;
c) optionally addition of 5-60 wt. %, in particular 10-60 wt. %, preferably 20-55 wt. %, more preferably 30-50 wt. %, of stabilizers and optionally further components;
d) mixing of reagents, perfumes, optionally stabilizers and optionally further components, so that the elastomeric, in particular cross-linked, polymer matrix is formed;
e) shaping a hollow body, in particular by means of a rotational method [centrifugal (casting) method] using the mixture manufactured in step d), wherein the percentages by weight in each case refer to the total weight of the hollow body.

A preferred method according to the invention is characterized by the fact that the cross-linker is a substance with at least one function group selected from the group consisting of epoxy resins, isocyanates, anhydrides and acrylates.

A particularly preferred method for producing a hollow body according to the invention uses DESMODUR N-3300 as the cross-linker.

A further particularly preferred method according to the invention for producing a hollow body according to the invention uses a rotational method for producing a hollow sphere, in which the speed of rotation is set such that the polymer matrix is still able to "run" ("flow"). It is up to the person skilled in the art to select an appropriate speed of rotation, so that the coating does not take place on a single side (single-sided coating would be a risk if the speed were too low), and so that an even coating is guaranteed (at excessive speeds even coating is not guaranteed). The person skilled in the art will be guided here to by methods with which he/she is familiar, for example from the production of Christmas tree baubles.

For the applications according to the invention and the methods according to the invention, the respective embodiments of the hollow bodies according to the invention described above (preferred or particularly preferred) apply by analogy.

In quantitative considerations of the composition of hollow bodies according to the invention, a substance contained, if it can be classified under two components, will be classified under the component that has been mentioned first above (e.g.: if with the substance it is a perfume which is also a stabilizer, this substance will be classified with the perfumes).

The following examples specify a number of hollow bodies according to the invention.

The names Sylvaclear® and Dowanol® are trademarks of the respective manufacturers.

Example 1

| Ingredients | Chemical name/ classification | Weight percent [%] |
|---|---|---|
| 188178 Blues | Perfume oil (Symrise) | 20.00 |
| Dowanol DPM | 1-(2-methoxypropoxy)-2-propanol | to 100.00 |
| Sylvaclear IM 700 | Polyamine | 26.40 |
| Sylvaclear IM 800 | Polyamine | 0.031 |

-continued

| Ingredients | Chemical name/ classification | Weight percent [%] |
|---|---|---|
| D&C Red No. 10 | 1-(4-(penylazo)phenylazo)-2-naphtol | 1.50 |
| Desmodur N-3300 | Aliphatic isocyanate | 3.60 |

Example 2

| Ingredients | Chemical name/ classification | Weight percent [%] |
|---|---|---|
| 382065 Sensitiv | Perfume oil (Symrise) | 20.00 |
| Dowanol DPM | 1-(2-methoxypropoxy)-2-Propanol | to 100.00 |
| Sylvaclear IM 700 | Polyamine | 10.40 |
| Sylvaclear IM 800 | Polyamine | 16.40 |
| Titanium dioxide | Titanium dioxide | 1.50 |
| Talcum | Talcum | 9.00 |
| Desmodur N-3300 | Aliphatic isocyanate | 3.60 |

Example 3

| Ingredients | Chemical name/ classification | Weight percent [%] |
|---|---|---|
| 228151 Lemonfreak | Perfume oil (Symrise) | 30.00 |
| Dowanol TPnB | Tripropylene glycol n-butyl ether | to 100.00 |
| Sylvaclear IM 700 | Polyamine | 13.20 |
| Sylvaclear IM 800 | Polyamine | 13.20 |
| Perlglanzpigment Gold BB | Pigment (Merck) | 0.10 |
| Desmodur N-3300 | Aliphatic isocyanate | 3.60 |

Production:

The hollow body is produced by mixing all the components except for the cross-linker (e.g. Desmodur N-3300). Following addition of the cross-linker, rapid and thorough mixing must again take place. The speed of hardening will vary according to the perfume oil and the mixing of the polymer components.

Figure 1:
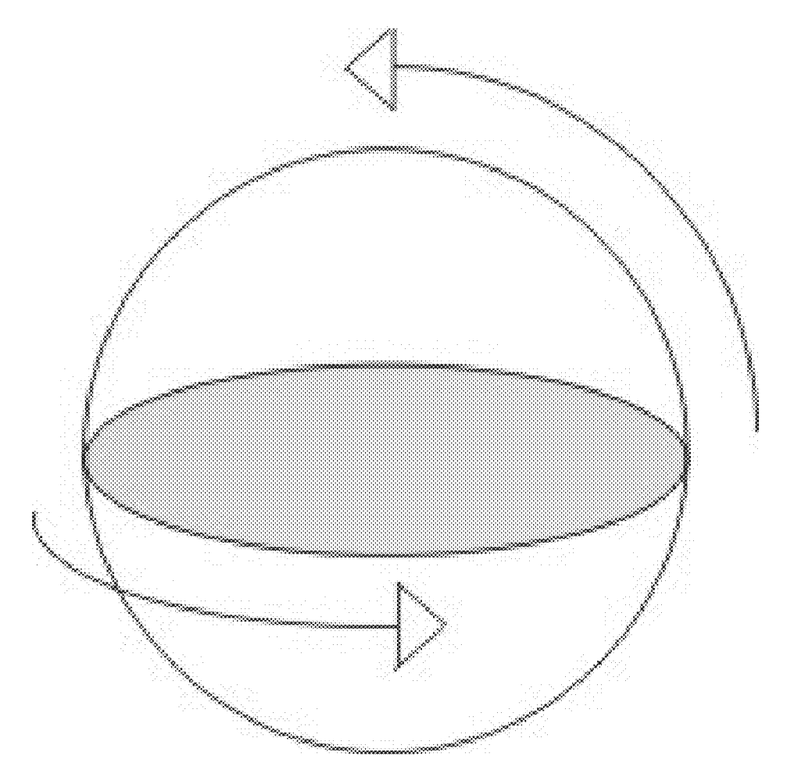
FIG. 1 shows a spherical mould used to produce a hollow body of the instant disclosure. The arrows indicate the 2 directions in which the machine simultaneously rotates to evenly coat the spherical mould with the polymer matrix.

In order to produce this hollow body it is necessary to coat the inside of the body at all points with the most even possible thickness. As a result of this, in the middle of the body to an air-filled space is created. The stability of the hollow body can be influenced through the layer thickness. The layer thickness is adjusted by means of the ratio of the filled polymer matrix quantity to the mould diameter. The mould used for the hollow mould is, for example, a polyacrylate mould or a polyethylene mould which is separated at its centre by a cut edge as shown in FIG. 1. One mould half is filled with the polymer matrix. Then the two mould halves are combined to form the complete mould and clamped in a machine. The machine displaces the spherical mould with the filled polymer matrix simultaneously through at least 2 axes in rotation.

The speed of rotation here must be set so that "running" ("flowing") of the polymer matrix is still possible. If the speed is too high even coating is not guaranteed. If the speed is too low the coating will only be on one side. The rotation is maintained throughout the hardening process. Once the hardening process is complete the mould is separated at the cut edge and the polymer shape is removed.

The invention claimed is:

1. A perfume-containing body enclosing a hollow space on all sides comprising
    an elastomeric polymer matrix; and
    one or more perfumes stored in the polymer matrix, wherein a total quantity of the one or more perfumes is 10-75 wt. %, with reference to a total weight of the perfume-containing body,
wherein
    the perfume-containing body has a total volume of 5-8,181 $cm^3$ at 25° C. and 1,013 mbar,
and
    a thickness of the perfume-containing body enclosing the hollow space on all sides at any point is 0.25-20 mm.

2. The perfume-containing body as claimed in claim 1, wherein the perfume-containing body is suitable for use in a laundry drier and/or in a dishwashing machine.

3. The perfume-containing body as claimed in claim 1, wherein the perfume-containing body's structural integrity remains intact after 5 or more standard drying cycles of a laundry drier or 10 or more standard dishwashing cycles of a dishwasher.

4. The perfume-containing body as claimed in claim 1, further comprising 5-60 wt. % of one or more stabilizers, with reference to the total weight of the hollow perfume-containing body, wherein the one or more stabilizers are stored in the elastomeric polymer matrix.

5. The perfume-containing body as claimed in claim 4, wherein each stabilizer, independent of any further stabilizer, if present, is pourable at 25° C. and 1,013 mbar and has a boiling point of greater than or equal to 180° C. at 1,013 mbar, or
    is solid and is selected from the group consisting of clay minerals and inorganic pigments.

6. The perfume-containing body as claimed in claim 4, wherein 30-50 wt. % of the one or more stabilizers, with reference to the total weight of the perfume-containing body, is stored in the elastomeric polymer matrix.

7. The perfume-containing body as claimed in claim 4, wherein each stabilizer, independent of any further stabilizer, if present, is pourable at 25° C. and 1,013 mbar, and is selected from the group consisting of phthalic acid esters, paraffins, polyalkylene glycols, polyalkylene glycol ethers and polyalkylene glycol esters,
    or
    is solid and is selected from the group consisting of talcum, chalk, calcium sulfate, calcium carbonate, bentonite, zinc oxide, titanium dioxide and montmorillonite.

8. The perfume-containing body as claimed in claim 1, wherein the total quantity of the perfumes stored in the elastomeric polymer matrix is 10-50 wt. % with reference to the total weight of the perfume-containing body.

9. The perfume-containing body as claimed in claim 1, wherein the perfume-containing body comprises 40 wt. % or more of the total quantity of perfumes originally present in the perfume-containing body after 5 standard drying cycles of a laundry drier, or after 5 standard dishwashing cycles of a dishwasher.

10. The perfume-containing body as claimed in claim 1, wherein the perfume-containing body releases 50 mg or more of perfumes for each standard laundry drier cycle or for each standard dishwashing cycle.

11. The perfume-containing body as claimed in claim 1, wherein the elastomeric polymer matrix is cold cross-linked.

12. The perfume-containing body as claimed in claim 1, wherein the elastomeric polymer matrix comprises a product of the reaction i) of a cross-linker selected from the group consisting of epoxy resins, isocyanates, anhydrides and acrylates
with
ii) at least one polyamine.

13. The perfume-containing body as claimed in claim 1, wherein the elastomeric polymer matrix comprises a product of the reaction of
   i) 2-5 wt. % of a cross-linker selected from the group consisting of epoxy resins, isocyanates, anhydrides and acrylates,
   with
   ii) 10-35 wt. % of at least one polyamine, wherein the wt. %, in each case, references the total weight of the perfume-containing body.

14. The perfume-containing body as claimed in claim 12, wherein the at least one polyamine is pourable at 25° C. and 1,013 mbar.

15. The perfume-containing body as claimed in claim 14, wherein the elastomeric polymer matrix comprises a product of the reaction of
   i) 2-5 wt. % of a cross-linker selected from the group of isocyanates,
   with
   ii) 15-30 wt. % of at least one polyamine,
wherein the wt. %, in each case, references the total weight of the perfume-containing body.

16. The perfume-containing body as claimed in claim 1, wherein the volume of the hollow space is 40 vol. %-98 vol. %, with reference to the total volume of the perfume-containing body at 25° C. and 1,013 mbar.

17. A method of applying a scent to laundry, and/or for scenting dishwasher air comprising using the perfume-containing body as claimed in claim 1 during a drying process in a laundry drier and/or during a dishwashing process of a dishwasher, wherein the perfume-containing body is suitable for repeated use.

18. A method for producing the perfume-containing body as claimed in claim 1 comprising:
   a) preparing at least one reagent for producing an elastomer;
   b) adding 10-75 wt. % of one or more perfumes;
   c) optionally adding 5-60 wt. % stabilizers and optionally adding further components;
   d) forming the elastomer by mixing the at least one reagent, one or more perfumes, and stabilizers and further components, if present; and
   e) optionally using a rotational method to shape a hollow body from the mixture manufactured in step d),
   wherein the wt. % in each case refers to the total weight of the perfume-containing body.

19. The perfume-containing body as claimed in claim 1, wherein the thickness of the perfume-containing body enclosing the hollow space on all sides at any point is 1-8 mm.

20. The perfume-containing body as claimed in claim 1, wherein the perfume-containing body's structural integrity remains intact after 10 or more standard drying cycles of a laundry drier.

* * * * *

UNITED STATES PATENT AND TRADEMARK OFFICE
CERTIFICATE OF CORRECTION

PATENT NO. : 8,334,252 B2
APPLICATION NO. : 12/958821
DATED : December 18, 2012
INVENTOR(S) : Wiedemann et al.

It is certified that error appears in the above-identified patent and that said Letters Patent is hereby corrected as shown below:

In the Claims:

At column 20, claim number 4, line number 25, should be read as follows:

reference to the total weight of the ~~hollow~~ perfume-contain-

Signed and Sealed this
Fourteenth Day of May, 2013

Teresa Stanek Rea
*Acting Director of the United States Patent and Trademark Office*